United States Patent
Heyman et al.

(10) Patent No.: US 9,027,562 B1
(45) Date of Patent: *May 12, 2015

(54) FLOW METERING CONNECTOR AND SYSTEM FOR OXYGEN OR AIR FLOW SUPPLY TO NASAL CANNULA

(75) Inventors: Arnold M. Heyman, Los Angeles, CA (US); Craig R. McCrary, Valencia, CA (US); Thomas R. Thornbury, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 376 days.

This patent is subject to a terminal disclaimer.

(21) Appl. No.: 12/931,880

(22) Filed: Feb. 14, 2011

(51) Int. Cl.
*A61M 15/08* (2006.01)
*A62B 7/00* (2006.01)
*A61M 16/06* (2006.01)

(52) U.S. Cl.
CPC ....... *A61M 16/0672* (2014.02); *A61M 2240/00* (2013.01)

(58) Field of Classification Search
USPC ............. 128/202.27, 206.11, 207.18; 285/70, 285/125.1, 131.1, 132.1, 133.11; 403/169, 403/177

See application file for complete search history.

(56) References Cited

U.S. PATENT DOCUMENTS

| | | | | |
|---|---|---|---|---|
| 3,726,275 | A * | 4/1973 | Jackson et al. | 128/207.18 |
| 4,633,890 | A * | 1/1987 | Carden | 128/202.27 |
| 4,827,921 | A * | 5/1989 | Rugheimer | 128/202.27 |
| 4,995,384 | A * | 2/1991 | Keeling | 128/207.18 |
| 6,763,832 | B1 * | 7/2004 | Kirsch et al. | 128/207.18 |
| 7,188,624 | B2 * | 3/2007 | Wood | 128/207.18 |
| 7,328,703 | B1 * | 2/2008 | Tiep | 128/207.18 |
| 2006/0108792 | A1 * | 5/2006 | Takasaki et al. | 285/131.1 |
| 2008/0121230 | A1 * | 5/2008 | Cortez et al. | 128/204.17 |

* cited by examiner

*Primary Examiner* — Kristen Matter
(74) *Attorney, Agent, or Firm* — William W. Haefliger

(57) ABSTRACT

A connector for connecting an oxygen input flow duct with two narrowed oxygen output flow ducts, is provided thereby to meter oxygen flow to nasal cannula, and includes a hollow body having a relatively large flow input chamber sized for telescopic interfit with the input flow duct, the body having two relatively smaller flow output chambers sized for telescopic interfit with the respective two output flow ducts. The two output chambers have direct and like-sized communication with the input chamber whereby input flow is equally divided into two output flow streams.

12 Claims, 4 Drawing Sheets

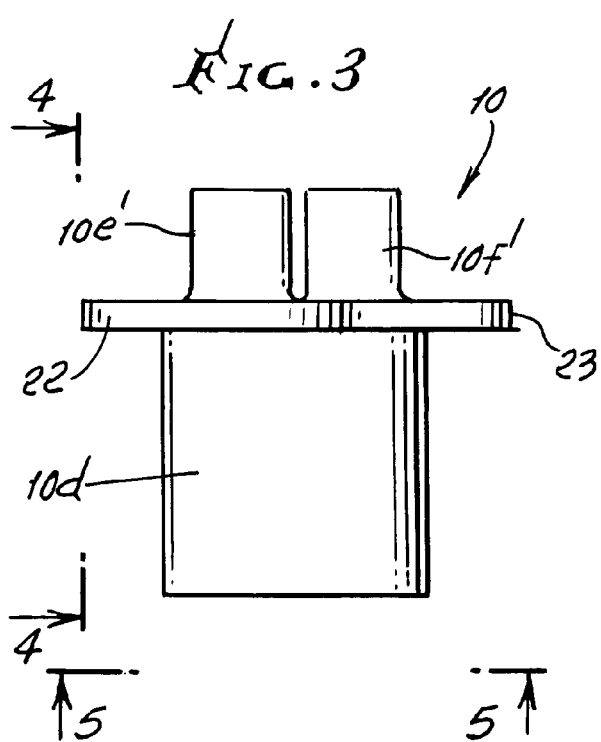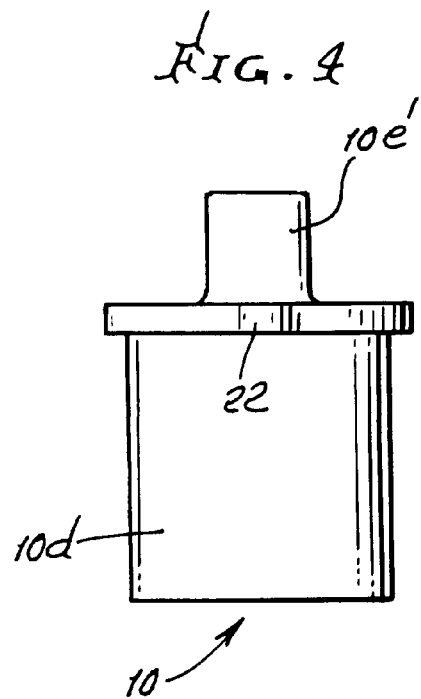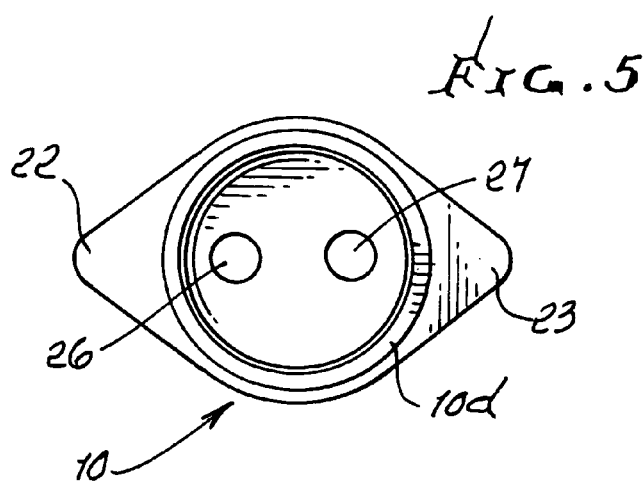

FLOW METERING CONNECTOR AND SYSTEM FOR OXYGEN OR AIR FLOW SUPPLY TO NASAL CANNULA

BACKGROUND OF THE INVENTION

This invention relates generally to respiratory support apparatus, and more particularly to efficient delivery of oxygen or air to nasal cannula.

There is need for improvements in non-invasive respirator support apparatus and methods. More particularly, there is need for such improved apparatus for delivering oxygen or air to nasal cannula, and particularly to such cannula used in or for infant therapy. There is also need for the efficient, compact, highly useful flow control apparatus providing improvements in modes of operation and results characterized by the present invention.

SUMMARY OF THE INVENTION

It is a major object of the invention to provide improved nasal therapy flow control or metering apparatus and method meeting the above needs. Basically, the improved apparatus embodies a flow metering connector for connecting an oxygen or air input flow duct with two narrowed output flow ducts, thereby to accurately meter air or oxygen flow to nasal cannula. The connector comprises:

a) a hollow body having a relatively large flow input chamber sized for telescopic interfit with an input flow duct, b) the body having two relatively smaller flow output chambers sized for telescopic interfit with the respective output flow ducts, c) the two output chambers having direct and like-sized communications with said input chamber, whereby input flow is equally and efficiently divided into two output flow streams.

As will be seen, the apparatus preferably comprises a single-piece body forming the chambers as referred to. A first portion of the body forms the input chamber and has an outer lateral diameter $d_1$, and a second portion of said body forms the output chambers, that have lateral external dimension $d_2$, where $d_1$ exceeds $d_2$. The output chambers typically extend at opposite sides of a plane containing an axis of the input chamber.

Another object is to provide narrowed flow metering passages in the unitary body, communicating between said input chamber and said output chambers. Such passages typically have like cylindrical bores, and equal lengths, whereby venturi type control of dual output flows is established.

Yet another object includes provision of an input duct sealingly connected with said input chamber, and the output ducting is sealingly connected with said two output chambers; and nasal cannula are typically employed in communication with the two output ducts, as will be seen.

A further object includes provision, integrally with the connector, of two wings such as flanges located outwardly of a flow junction between the input and output chambers, for manual grasping, and efficient manipulation of all ducting is enabled.

An added object is to provide the connector body with a wall extending about the input chamber, the wall having an external surface that tapers endwise directionally toward said output chambers, for endwise progressively increasing sealing, push-on engagement with the input duct.

Another object is to provide the connector body with output chamber interior surfaces that taper endwise directionally toward said input chamber, for endwise progressively increasing sealing push-on engagement with the output ducts.

These and other object and advantages of the invention, as well as the details of an illustrative embodiment, will be more fully understood from the following specification and drawings, in which:

DRAWING DESCRIPTION

FIG. 3 is an elevation showing a side of the cannula;

FIG. 4 is a view taken on lines 4-4 of FIG. 3;

FIG. 5 is a plan view taken on lines 5-5 of FIG. 3;

DETAILED DESCRIPTION

Figure 1:
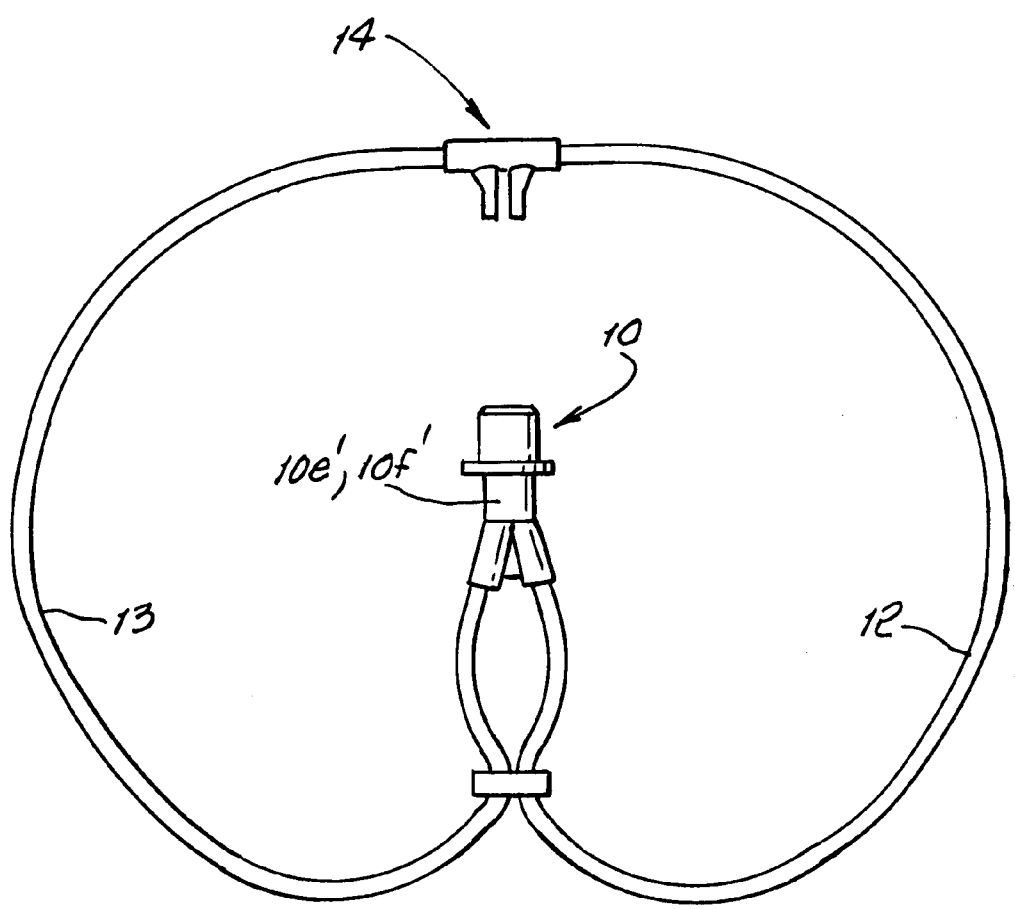
FIG. 1 is a view of apparatus incorporating the invention.
Figure 2:
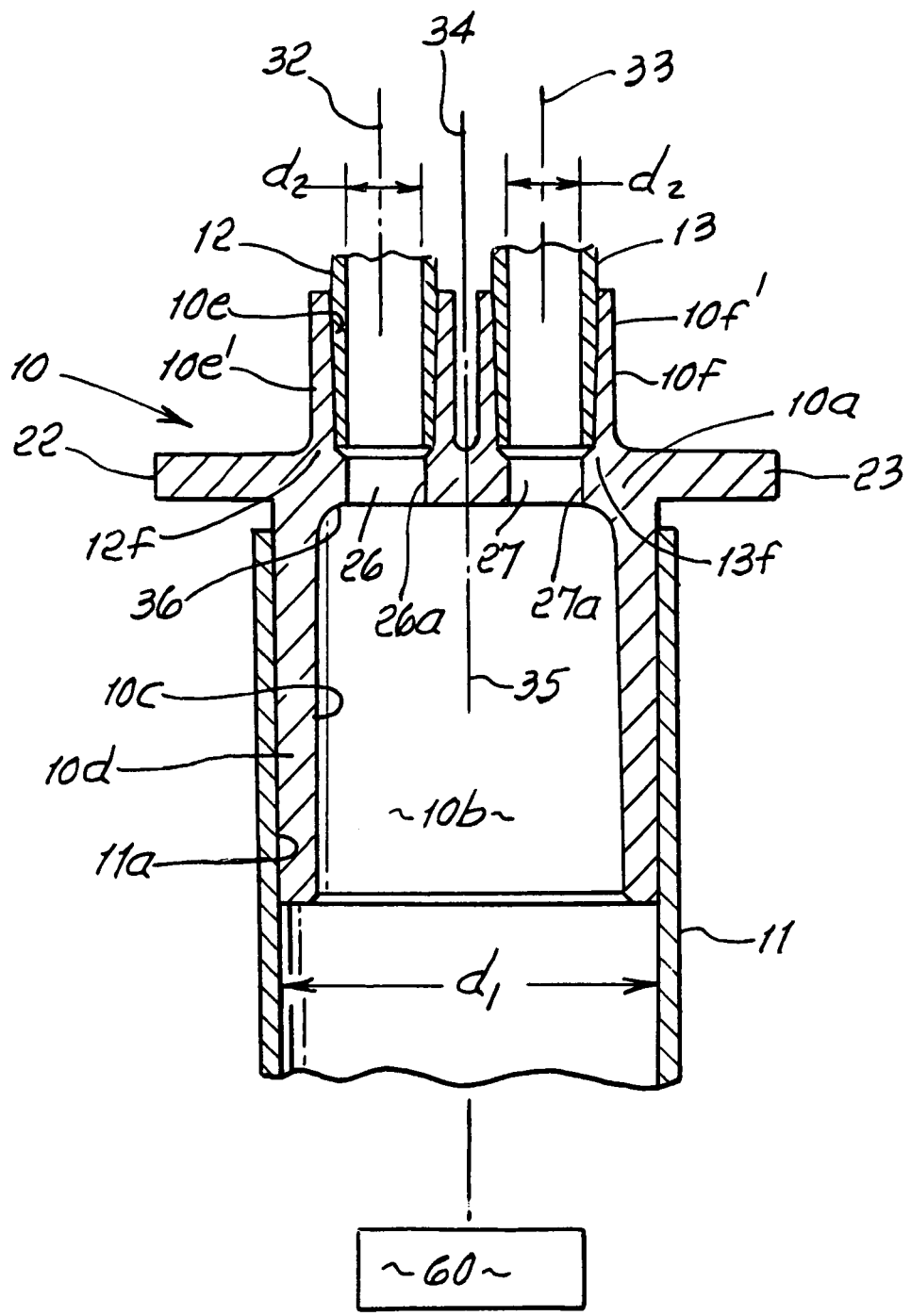
FIG. 2 is an enlarged section taken through a flow metering connector.

In the preferred form of the apparatus, the connector 10 is configured for connecting to an oxygen or air input flow duct 11 of bore diameter $d_1$, and to two narrowed output flow ducts 12 and 13 of bore diameter $d_2$. The connector operates as a flow metering device for accurately controlling flow to nasal cannula means 14, via like ducts 12 and 13. The single piece connector body 10a avoids flexing of its component parts, in use, for enhanced safety, while enabling manipulative positioning of all ducts, relative to an infant.

Body 10a defines a relatively large flow input chamber 10b with tapered bore 10c of wall 10d sized for push-on telescopic interfit with input flow duct 11. That duct preferably fits over and is adhesively sealed to the tapered annular wall 10d as shown. Wall 10d of the body is integral with two wings or body flanges 22 and 23, used for manipulation as during duct connection to the body, or for positioning the body and ducts relative to the nasal region of an infant patient. Such wall 10d taper assures a tight endwise push-on interfit of the bore 11a of duct 11 with the tapered wall during assembly, and aids in preventing inadvertent disassembly.

Body 10a also has two relatively smaller flow output chambers 10e and 10f formed within body extents 10e' and 10f' that project endwise away from the flanges or wings, as shown. The chambers 10e and 10f have like bores that taper, slightly (less than 10°) directionally away from metering zones 26 and 27 that serve as junctions between chambers 10e and 10f and the input chamber 10b. Zones 26 and 27 have like bores 26a and 27a that are fixed and narrower than bores of 10e and 10f, compensating for uncontrolled or unknown bores of input and output ducts 11, 12 and 13 that interfit the body 10, and that affect flow rate. Junction zones 26 and 27 also serve to controllably and equally divide the input flow stream into two streams to flow via ducts 12 and 13 to cannula means 14.

It will be noted that, for enhanced control, the output chambers define axes 32 and 33 located at equal lateral distances from a plane 34 containing central axis 35 of the input chamber. Input chamber 11 has an inner annular end wall portion 36 that is concave i.e. a first curved surface and merges bore 10c of chamber 10b with the two junction passages 26 and 27; and there are similar reduced diameter annular wall portions 12f and 13f of chambers 12 and 13, that are concave i.e. body second curved surfaces and merge the discharge ends of passages 26 and 27 with the output ducts. Accordingly, dual venture effects are efficiently achieved with respect to the dual flows, for enhanced flow control.

Figure 6:
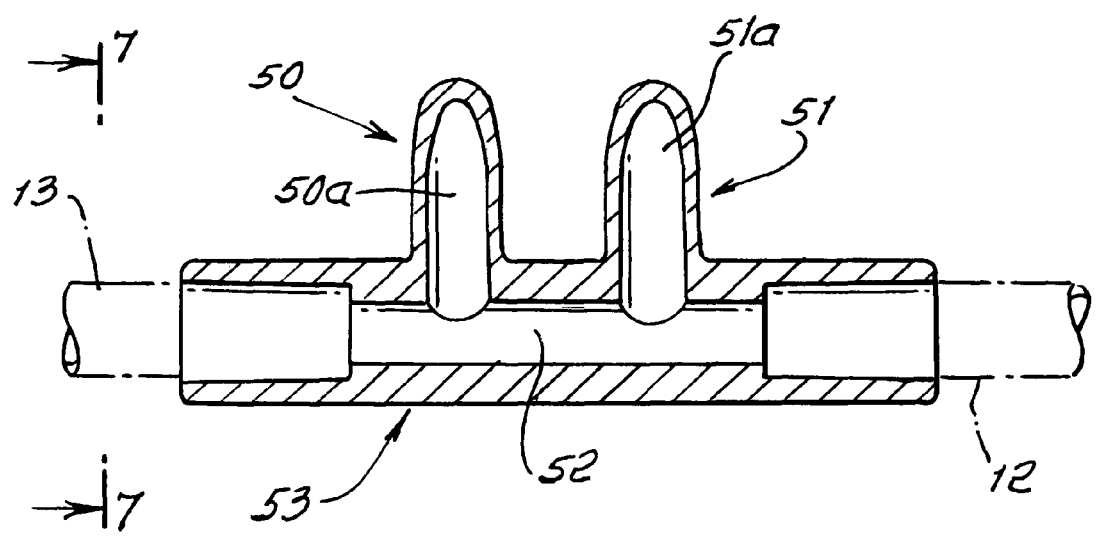
FIG. 6 is an enlarged section taken through modified nasal cannula structure.
Figure 7:
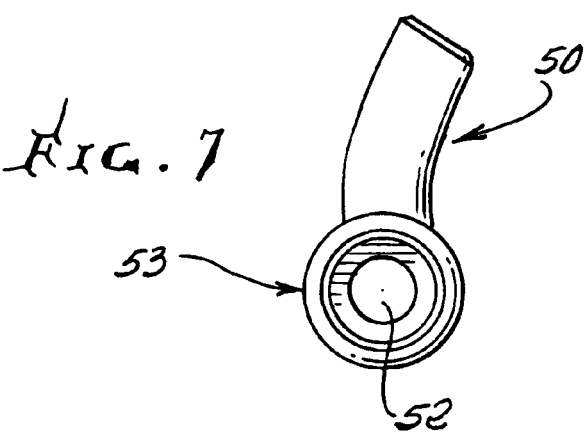
FIG. 7 is an end view taken on lines 7-7 of FIG. 6.

FIGS. 6 and 7 show nasal cannula 50 and 51 that are curved sidewardly away from passage 52 in a tubular body 53, for enhanced sealing with nostril passages, and comfort. The cannula have curved inner flow passages 50a and 51a, as shown. Tubing 12 and 13 connects with 53, as shown.

All flow tubing may be translucent, and may have identifying color, such as green color (for example indicating oxygen flow). The input flow duct 11 may be connected to pressurized oxygen flow supply apparatus 60.

What is claimed is:

1. A connector for connecting an oxygen input flow duct with two narrowed oxygen output flow ducts, thereby to meter oxygen flow to nasal cannula, comprising
   a) a hollow body having a relatively large flow input chamber sized for telescopic interfit with said input flow duct, said input chamber having an interior and having a diameter,
   b) the body having two relatively smaller flow output chambers sized for reception of and telescopic interfit with the respective output flow ducts, and located in direct and open alignment with the interior of said input chamber throughout the length thereof, said input chamber having substantially the same interior width throughout the length thereof,
   c) said two output chambers having direct and like-sized communication with said input chamber whereby input flow is equally divided into two output flow streams,
   d) the output flow ducts directly communicating with the entirety of the input flow duct proximate two intervening venturi passages defined by the connector, said input flow duct sealingly connected with said input chamber, and said output flow ducts sealingly connected with said two output chambers, said two venturi passages having overall width less than the diameter of said input chamber throughout the length thereof,
   e) said body having a wall extending about the interior of said input chamber, said wall having an internal surface that slightly tapers endwise directionally toward said output chambers to further define said interior width, for endwise progressively increasing sealing engagement with the input flow duct, said internal surface having said diameter that everywhere exceeds internal diameters defined by the flow output chambers,
   f) said output chambers have interior surfaces that taper endwise directionally toward said input chamber, for endwise progressively increasing sealing push-in engagement with the output flow ducts,
   g) and including nasal cannula in communication with said output flow ducts,
   h) there being a body first curved surface to guide flow from said flow input chamber into said venturi passages, and body second curved surfaces to guide flow from said venturi passages toward said output flow ducts.

2. The connector of claim 1 comprising a single-piece body.

3. The connector of claim 2 wherein a first portion of said body forms said input chamber and has an outer lateral diameter $d_1$, and a second portion of said body forms said output chambers, that have lateral external dimensions $d_2$, where $d_1$ exceeds $d_2$.

4. The connector of claim 1 wherein said connector includes two wings located outwardly of flow junctions between said input and output chambers.

5. The connector of claim 3 wherein said connector includes two wings located outwardly of said venturi passages at flow junctions between said input and output chambers.

6. The connector of claim 1 wherein the output chambers define axes at equal distances from a plane containing an axis of the input chamber.

7. The connector of claim 1 wherein there are narrowed flow metering passages defined by said venturi passages in said body, communicating between said input chamber and said output chambers.

8. The connector of claim 7 wherein said flow metering passages have like cylindrical bores, and lengths.

9. The connector of claim 7 wherein the connector has two wings located outwardly of and extending away from said flow metering passages.

10. The connector of claim 1 wherein said venturi passages are provided between said input and output chambers.

11. The connector of claim 1 wherein the output flow ducts comprise tubing connected with the nasal cannula.

12. The connector of claim 11, and wherein the nasal cannula projects sidewardly away from said tubing, and with lengthwise curvature.

* * * * *